United States Patent [19]

Shoults

[11] 4,132,740
[45] Jan. 2, 1979

[54] PREPARATION OF CARBORANYL SULFIDES

[75] Inventor: Royland D. Shoults, Fayetteville, N.C.

[73] Assignee: The United States of America as represented by the Secretary of the Army, Washington, D.C.

[21] Appl. No.: 293,257

[22] Filed: Oct. 3, 1972

[51] Int. Cl.$^2$ ............................................... C07F 5/02
[52] U.S. Cl. ................................. 260/606.5 B; 149/22
[58] Field of Search .................... 149/22; 260/606.5 B

[56] References Cited

U.S. PATENT DOCUMENTS 3,674,853   7/1972   Obenland et al. ............. 260/606.5 B

*Primary Examiner*—Leland A. Sebastian
*Attorney, Agent, or Firm*—Nathan Edelberg; Robert P. Gibson; Jack W. Voigt

[57] ABSTRACT

Carboranylmethyl alkyl sulfides are disclosed along with a process for preparation which process involves reacting decaborane with the propargyl alkyl sulfide in cyclohexane.

7 Claims, No Drawings

PREPARATION OF CARBORANYL SULFIDES

BACKGROUND OF THE INVENTION

Carborane and derivatives of carborane belong to a class of compounds known to be effective ballistic modifiers for obtaining high burning rates. A number of derivatives of carborane also serve as effective plasticizers in composite propellants. n-Hexylcarborane (NHC) has been used in propellant, however, the low yield of the process for preparation and the complex process for preparation contribute to the high cost of n-hexylcarborane. Similarly, other alkyl carboranes have been prepared with corresponding results of high costs due to complexities of processes and the low yields thereof. Although extensive efforts have been spent toward improving the NHC process, no significant increases in yields have been achieved.

A simpler process than the NHC process is desired to produce derivatives of carborane in higher yield to result in lower cost than NHC or similar alkyl carboranes. Therefore, an object of this invention is to provide a process for preparing derivatives of carborane which derivatives are suitable for use in propellant compositions to achieve very high burning rates.

Another object of this invention is to provide a simpler process to produce high yields of carborane derivatives that have desirable properties for propellant use.

SUMMARY OF THE INVENTION

A process for preparing carboranylmethyl alkyl sulfides has been discovered which process involves the reaction of decaborane with the appropriate propargyl alkyl sulfide in cyclohexane. The equation for the reaction is summarized below (equation 2). No added ligand is necessary, since the acetylenic sulfide serves this purpose. Equation (1) illustrates the process for preparation in high yields of propargyl alkyl sulfides employed in reaction (2) as the starting material for preparing the carboranylmethyl alkyl sulfide. The ethyl, propyl, isopropyl, butyl, and isobutyl derivatives were prepared and are represented by Compound I of equation (1) where R equals alkyl.

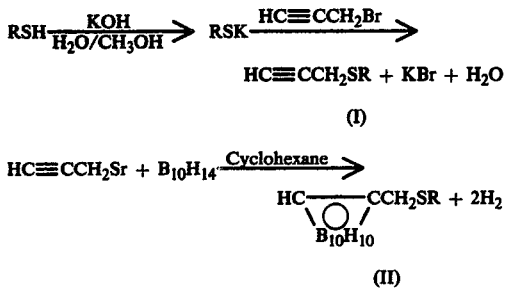

Compound II represents the carboranylmethyl alkyl sulfides of this invention, where R equals alkyl. The alkyl of this invention, represented by R, preferably contains from 2-4 carbon atoms; however, the alkyl can contain from 2-10 carbon atoms.

The compounds prepared in accordance with the process of this invention include: carboranylmethyl ethyl sulfide (CMES), carboranylmethyl n-propyl sulfide (CMPS), carboranylmethyl iso-propyl sulfide (CMIPS), carboranylmethyl n-butyl sulfide (CMBS), and carboranylmethyl iso-butyl sulfide (CMIBS). Other carboranylmethyl alkyl sulfides having longer chains and/or branched chains can be prepared by first preparing the appropriate propargyl alkyl sulfide by the process outlined above.

DESCRIPTION OF THE PREFERRED EMBODIMENT

The preparation of the carboranylmethyl alkyl sulfides of this invention involves the reaction of decaborane ($B_{10}H_{14}$) and the pertinent propargyl alkyl sulfide using cyclohexane as the reaction solvent.

Representative of the carboranylmethyl alkyl sulfides of this invention is carboranylmethyl ethyl sulfide (CMES) which is prepared by the preferred process set forth hereinbelow.

Preparation of CMES from Decaborane (1-mole scale)

NOTE: Caution should be exercised in working with decaborane and its derivatives, because of the toxic properties that may be harmful through inhalation as well as skin absorption. Consequently, the reactions associated with decaborane should be carried out in a well-ventilated hood.

Reagents:
(a) 127.3 gm (1.0 mol) of 96% decaborane
(b) 500 ml of cyclohexane (practical grade)
(c) 135.3 gm (1.35 mol) of propargyl ethyl sulfide (PES) (97.9% purity)

Procedure: The apparatus consists of a 1-liter round bottom flask equipped with a chilled water condenser (with Drierite tube), magnetic stirrer, heating mantle, and a bubbler connected to the condenser exit to follow the evolution of hydrogen. For some reactions the evolution of hydrogen is measured by means of a Wet-Test-Meter (Precision Scientific Co.). The decaborane (a) is placed in the flask followed by the addition of the solvent (b). The mixture is sitirred until most of the decaborane is dissolved and the PES (c) is added. The solution is brought to reflux temperatures (85° to 87° C.) and allowed to reflux 29 hours. Appropriate precautions should be taken for the evolution of hydrogen for largescale reactions. The incremental addition of PES may be employed. During the initial part of the reaction (several hours) the evolution of hydrogen is most prominent. After 28 hours the theoretical amount of hydrogen is evolved and essentially no decaborane is detectable in a sample subjected to gas chromatographic analysis. The crude reaction product solution is allowed to cool, transferred to a separatory funnel, washed two times with 300 ml of 10% potassium hydroxide, two times with 300 ml of water (saline solutions may be employed if any difficulty is encountered in separation). The product solution is transferred to simple distillation assembly and the volatile materials, including any excess propargyl ethyl sulfide (no effort was made to recover this material) are distilled (some foaming may occur) until the pot temperature reaches 110° C. The remaining volatiles are removed at reduced pressure (gradually reducing to 1 mm) and at a final pot temperature of 100° C. Finally, the product residue is crude distilled at reduced pressure (0.5 mm) to obtain 175 gm (yield 80%) of product boiling at 110° C. to 130° C. The pot temperature is allowed to reach 160° C. before terminating the distillation.

Purification of the crude-distilled CMES for use in HTPB and fine AP-based propellants is carried out as follows: The CMES is placed on a fairly efficient distillation column (12-inch Vigreux) and pyrolyzed under nitrogen at 150° to 160° C. for two hours, then allowed to cool somewhat, and distilled at reduced pressure (0.1 mm) to obtain a forerun (10.9 gm) boiling at 90° to 112° C. and a main fraction (158 gm) (representing a 72% yield based on decaborane) boiling at 112° to 120° C. The purity is 98.7% (determined by gas chromatography using a Perkin-Elmer 800 with a SR model Sargent Recorder and a 6-ft SF 96-DC 710 packed column). Density ($d_4^{27}$) 1.022; mp, −5° C., D.T,A,, endotherm at 326° C.; KMnO$_4$ test, 300 μl required for thirty minutes.

Elemental Analyses: Calc'd for $C_5H_{18}B_{10}S$: C, 27.50; H, 8.31; B, 49.51; S, 14.68. Found: C, 27.8, H, 8.50; B, 49.6: S, 15.5.

Infrared (neat) 3.36 (carboranyl CH) and 3.84 (B-H) $CM^{-1}$; H'NMR; δ1.23 (t, 3, J = 7 Hz, —CH$_3$), δ2.61 (q, 2, J = 7 Hz, CH$_2$), δ4.05 (bs, 1, carboranyl CH). The proton NMR spectrum is measured in CDCl$_3$ employing a Varian A-60 spectrometer and tetramethylsilane as the internal standard.

Since proparyl alkyl sulfide is an essential starting material for use in accordance with the process of this invention several processes were considered for meeting the current needs. The alkylation of mercaptans has been accomplished by (1) coupling alkyl halides, (2) alkyl sulfates, or (3) esters of sulfonic acids with sodium or potassium mercaptides in aqueous or ethanolic solutions, illustrated by the reactions:

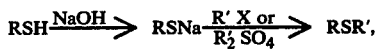

Where R' equals a lower alkyl and X equals halides. Additional information about the reaction type (1), above, is included in the following:

Shriner, Struck, and Jorison, *J. Am. Chem. Soc.*, 52, 2066 (1930);

Kirner and Richter, *J. Am. Chem. Soc.*, 51, 3135 (1929);

Kipnis and Ornfelt, *J. Am. Chem. Soc.*, 71, 3571 (1949); and

Fehnel and Carmack, *J. Am. Chem. Soc.*, 71, 92 (1949).

Additional information about the reaction type (2), above is included in the following:

Vogel, *J. Chem. Soc.*, 1822 (1948); and,

Tarbell And Fukushima, *J. Amer. Chem. Soc.*, 68, 1458 (1946).

Additional information about the reaction type (3), above, is included in the following:

Gilman and Beaber, *J. Am. Chem. Soc.*, 47, 1449 (1925).

Attempts to prepare propargyl ethyl sulfide (III) by reaction of propargyl bromide, sodium hydroxide, and ethyl mercaptan in ethanol resulted in inconsistent yields (max 75%) and the formation of undesirable impurities.

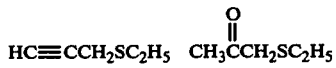

III        IV

The hydration product, acetonyl ethyl sulfide (IV) (bp, 42–46° C. at 5 mm), was identified as one of the main impurities [H'NMR spectrum measured at 60 Hz in CDCl$_3$, Me$_4$S, as std. δ1.23 (t, J = 7 Hz, —CH$_3$), δ2.28 (s, CH$_3$—C=O), δ2.52 (q, J = 7 Hz, —CH$_2$CH$_3$), δ3.25

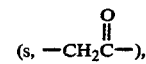

ir 5.83μ, C=O].

The above method also has the disadvantage of requiring large volumes of water in order to recover the product from the ethanol solvent. Alkylations with alkyl halides in aqueous solutions are not reported.

Propargyl ethyl sulfide is prepared by a simplified process (described below) in 85 to 90% yields by reaction at ambient temperatures of propargyl bromide, ethyl mercaptan, and sodium or potassium hydroxide in a water-methanol (2:1) solution. Reaction temperature is critical, in that at elevated temperatures isomerization of the acetylene to allene is pronounced. For example, at reflux temperature (80° C.) formation of approximately 50% allene ethyl sulfide (identified by infrared and proton NMR) occurred in 2.5 hours. No isomerization is observed below 35° C. which is contrary to the teachings of an earlier report, Guy Pourcelot, Paul Codiot, and Antonine Willemart (Ecole Nationale Super Paris) Compt. rend., 252, 1630-2 (1961).

Preparation of Propargyl Ethyl Sulfide by a Simplified Process

Potassium hydroxide (202.0 gm, 3.6 mol) is added to a stirred solution of water (600 ml) and methanol (30 ml) contained in a 3-liter, 3-necked flask equipped with a thermometer, dropping funnel, mechanical stirrer, condenser and water bath. The resulting solution, is heated to 60° C., cooled to 25° C. and ethyl mercaptan (214.3 gm, 3.45 mol) is added (mild exotherm). The reaction temperature is then adjusted to 25° C. by means of an ice water bath and propargyl bromide (57 gm, Columbia Organic Chemical, 96% purity, 2.88 mol) is added (exotherm) via the dropping funnel over 1.15 hours while the temperature is maintained at 25° to 35° C. (max). After the addition is completed the mixture is stirred 24 hours at room temperature (propargyl bromide content, by gc, trace), then transferred to a separatory funnel, the aqueous layer (lower) drained, the crude product layer is washed two times with 300 ml of water, dried with a small quantity (15 gm) of magnesium sulfate, and filtered. Finally, the product is distilled at reduced pressure (53 mm) through a 10-inch Vigreux column to obtain a forerun (7.7 gm) and a main cut (245 gm) boiling at 56° to 59° C. Yield (main cut), 85%; purity (gas chromatography), 97.7% (propargyl bromide - trace). Reported (Pourcelot et al, supra) bp, 67° C. at 76 mm. IR (neat): 3μ, H-C≡; 5.3μ, C=C; Proton NMR: measured at 60 Hz in CDCL$_3$, ME$_4$S: at std. δ1.28 (S, J = 7 Hz, —CH$_3$), δ2.71 (quartet, J = 7 Hz, —CH$_2$— adjacent to —CH$_3$), δ2.73 (multiplet, H-C≡C) δ3.26 (d, J = 3 Hz, —CH$_2$— adjacent to C≡C).

The carboranylmethyl alkyl sulfides of this invention serve as plasticizers for propellants and are very effective burning-rate promoters. These compounds are used with other propellant ingredients comprised of polybutadiene binder, bonding agent, ammonium perchlorate oxidizer, aluminum metal fuel, and a crosslinking agent appropriate for reaction with the binder, such as toluene diisocyanate crosslinking agent when hydroxyl terminated polybutadiene is the binder material or epoxy crosslinking agent or crosslinking agents such as MAPO (brand name for tris[1-(2-methyl)-aziridinyl]-phosphine oxide) when carboxy terminated polybutadiene is the binder material.

I claim:

1. A process for preparation of carboranylmethyl alkyl sulfides comprising:
   (a) combining a predetermined amount of decaborane with a predetermined amount of cyclohexane to form a mixture in a suitable reaction container that is provided with means for heating, means for cooling, and means for stirring, said container being equipped with a condenser and means for venting of gaseous reaction products;
   (b) stirring said decaborane and cyclohexane until most of the decaborane is dissolved;
   (c) adding a predetermined amount, including an excess of the theoretical amount, of a propargyl alkyl sufide to said mixture, said propargyl alkyl sulfide having the formula: $HC{\equiv}CCH_2SR$, where R equals an alkyl group having from 2 to 10 carbon atoms;
   (d) refluxing said mixture having said propargyl alkyl sulfide added thereto at a predetermined temperature range and for a predetermined period of time while reacting is accomplished and venting of gaseous reaction products, including hydrogen, is accomplished, said reacting forming a crude reaction product in solution;
   (e) cooling said crude reaction product in solution;
   (f) transferring said crude reaction product in solution to a suitable container for separating said crude reaction product;
   (g) washing said crude reaction product in solution a plurality of times with a 10% potassium hydroxide solution and followed by washing a plurality of times with a solution selected from water and saline solution to thereby effect separating of said crude reaction product that has been washed;
   (h) transferring the separated and washed crude reaction product in solution to a distillation assembly;
   (i) distilling the volatile materials, including any excess propargyl alkyl sulfide, until a temperature of about 110° C. is reached, and thereafter, continue distilling the remaining volatiles while gradually reducing the pressure to about 1 mm and while gradually reducing the temperature to about 100° C.; and
   (j) separating the reaction product by further distilling at a reduced pressure of about 0.5 mm and at a temperature from about 110° C. to about 160° C., said reaction product being a carboranylmethyl alkyl sulfide having the structure:

where R equals an alkyl group having from 2 to 10 carbon atoms.

2. The process of claim 1 wherein said predetermined amount of decaborane is about 1 mole; said predetermined amount of cyclohexane is about 500 milliliters; said predetermined amount of said propargyl alkyl sulfide including an excess of the theoretical amount is about 1.35 moles; and said refluxing is accomplished at said predetermined temperature range of about 85° C. to about 87° C. and for said predetermined period of time of about 29 hours.

3. The process of claim 2 wherein said propargyl alkyl sulfide is propargyl ethyl sulfide and said reaction product is carboranylmethyl ethyl sulfide having the structure:

4. The process of claim 1 wherein said propargyl alkyl sulfide is propargyl propyl sulfide and said reaction product is carboranylmethyl propyl sulfide.

5. The process of claim 1 wherein said propargyl alkyl sulfide is propargyl isopropyl sulfide and said reaction product is carboranylmethyl isopropyl sulfide.

6. The process of claim 1 wherein said propargyl alkyl sulfide is propargyl butyl sulfide and said reaction product is carboranylmethyl butyl sulfide.

7. The process of claim 1 wherein said propargyl alkyl sulfide is propargyl butyl sulfide and said reaction product is carboranylmethyl isobutyl sulfide.

* * * * *